United States Patent [19]

Ninomiya et al.

[11] Patent Number: 4,690,786

[45] Date of Patent: Sep. 1, 1987

[54] PROCESS FOR PRODUCING A MICROCAPSULE CONTAINING A LIQUID ACTIVE MATERIAL

[75] Inventors: Yasuo Ninomiya; Chiaki Komamura; Yoshikazu Musa, all of Osaka, Japan

[73] Assignee: Nitto Electric Industrial Co., Ltd., Osaka, Japan

[21] Appl. No.: 832,602

[22] Filed: Feb. 24, 1986

Related U.S. Application Data

[63] Continuation-in-part of Ser. No. 608,834, May 10, 1984, abandoned.

[30] Foreign Application Priority Data

Dec. 12, 1983 [JP] Japan .................................. 58-234688

[51] Int. Cl.[4] .......................... A61K 9/52; B01J 13/02
[52] U.S. Cl. ...................................... 264/4.6; 424/84; 424/408; 424/462; 424/497; 428/402.22; 428/402.21; 514/963
[58] Field of Search .................... 264/4.6; 428/402.22; 424/33, 84, 408, 462, 497

[56] References Cited

U.S. PATENT DOCUMENTS

| | | | |
|---|---|---|---|
| 3,338,991 | 8/1967 | Insalaco et al. | 264/5 X |
| 3,409,461 | 11/1968 | Mehlo et al. | 427/215 |
| 3,413,172 | 11/1968 | Osborne | 156/334 |
| 3,830,750 | 8/1974 | Wellman | 428/402.22 X |
| 4,286,020 | 8/1981 | Himel et al. | 428/407 |
| 4,323,556 | 4/1982 | DalMoro et al. | 424/84 |

FOREIGN PATENT DOCUMENTS

| | | |
|---|---|---|
| 67533 | 12/1982 | European Pat. Off. . |
| 1294932 | 5/1969 | Fed. Rep. of Germany . |
| 367654 | 7/1982 | Fed. Rep. of Germany . |
| 861309 | 10/1940 | France . |
| 2430259 | 7/1979 | France . |
| 196911 | 3/1984 | New Zealand . |
| 1053500 | 1/1967 | United Kingdom . |
| 1090971 | 11/1967 | United Kingdom ........... 427/213.36 |
| 2013610 | 8/1979 | United Kingdom . |
| 2104033 | 3/1983 | United Kingdom . |

*Primary Examiner*—Richard D. Lovering
*Attorney, Agent, or Firm*—Sughrue, Mion, Zinn, Macpeak, and Seas

[57] ABSTRACT

A process for producing a microcapsule containing a liquid active material is described, comprising the steps of:

(1) dissolving in an organic solvent a polymer, esp. a polysulfone and an active material which has a limited solubility of about 0.01 to about 2 parts by weight in 100 parts by weight of said polymer and which is liquid at room temperature, the amount of said liquid active material added being more than the limited solubility and being about 2 to about 250 parts by weight per 100 parts by weight of the polymer and said organic solvent being capable of dissolving the respective components and being more volatile than said active material;

(2) atomizing the resulting solution through a nozzle into a gaseous atmosphere to form a mist of tiny liquid droplets; and (3) removing the solvent from the droplets by evaporation so as to provide a microcapsule having the liquid active material confined by the wall of said microcapsule made of the polymer.

16 Claims, 6 Drawing Figures

PROCESS FOR PRODUCING A MICROCAPSULE CONTAINING A LIQUID ACTIVE MATERIAL

CROSS REFERENCE TO THE RELATED APPLICATION

This application is a continuation-in-part application of application Ser. No. 608,834, filed on May 10, 1984, entitled "PROCESS FOR PRODUCING A MICROCAPSULE CONTAINING A LIQUID ACTIVE MATERIAL", now abandoned.

FIELD OF THE INVENTION

The present invention relates to a process for producing a microcapsule containing a liquid active material. More particularly, the invention relates to a process for producing a microcapsule which is capable of releasing a chemically labile liquid active material at a substantially controlled rate while maintaining the material stable over a long period of time.

BACKGROUND OF THE INVENTION

Several processes are known for producing a microcapsule comprising a polymer wall which confines an active material that is liquid at room temperature or a liquid solution of such active material. According to a typical method, a preformed polymer is used as a wall-forming material and a polymer emulsion is dried in water. If the active material is to be encapsulated as an aqueous solution, the following method is generally used: a film-forming polymer is dissolved in an organic solvent having a lower boiling point than that of water, and the aqueous solution of the active material is added to the polymer solution to make a primary water-in-oil (W/O) emulsion. The emulsion is added under agitation to an aqueous solution containing a protective colloidal substance such as gelatin or surfactant, thereby forming a secondary (W/O)/W emulsion. This emulsion is heated or placed under vacuum to remove the organic solvent and provide a microcapsule having the active material confined by the polymer wall. Such procedures are described in U.S. Pat. No. 3,523,906.

If the active material is an oil which is either insoluble or poorly soluble in water or if a solution of such oil is used as the active material, the following method may be used: the active material and a hydrophobic film-forming polymer that is not miscible with this active material are dissolved in an organic solvent capable of dissolving the two components but which is poorly soluble in water and has a lower boiling point than that of water; the resulting solution is dispersed in an aqueous solution containing a protective colloidal substance such as gelatin or surfactant, thereby providing an O/W emulsion; the emulsion is then heated or placed under vacuum to remove the organic solvent and produce a microcapsule having the active material confined by the polymer wall. Such procedures are described in U.S. Pat. Nos. 3,660,304 and 3,960,757.

These prior art methods of encapsulation have a relatively small latitude for the selection of the film-forming polymer, because it depends entirely upon whether the active material to be encapsulated is oily or aqueous. Furthermore, these methods involve the step of forming the primary or secondary emulsion, and the quality of the secondary emulsion produced is not always satisfactory. As a further disadvantage, the solvent used must be water-insoluble and a long period of time is generally required for removing the solvent.

Pest control with minimum disturbance to the ecosystem is becoming an increasingly important goal, and one method effective for this purpose is by slowly releasing sex pheromones into air. Sex pheromones are secreted by glands in the terminal segments of the abdomen of female insects, and can be used to attract male insects into traps where they are killed, or interfere with their normal mating. Microcapsules prepared by the prior art methods are of course effective to some extent for the purpose of slowly releasing pheromones. However, most pheromones are chemically labile because they contain unsaturated bonds or aldehyde groups. Encapsulated pheromones, when exposed to ambient conditions, easily change to other substances which do not have the desired effect. Therefore, it has generally been difficult to prepare microcapsules from which pheromones can be slowly released while exhibiting their ability to attract males and interfere with mating over a long period of time. In particular, with the conventional method of encapsulation, microcapsules are formed in water, and the water or oxygen present in the microcapsules may accelerate the deterioration of the liquid active material, and in an extreme case, that active material may be lost into the water. Entrance of water into the microcapsule may also occur easily when the active material is an oil or a solution thereof.

SUMMARY OF THE INVENTION

The present invention has been accomplished in order to overcome the above mentioned defects of the prior art techniques of encapsulation.

An object of the present invention is to provide a novel process for producing a microcapsule containing a liquid active material, and is characterized by the following features: it permits a greater latitude for the selection of a film-forming material to confine the liquid active material; the microcapsule can be obtained without forming the primary or secondary emulsion as is required in the conventional techniques; and the microcapsule produced permits the release of a chemical labile liquid active material (e.g., an aldehyde containing pheromone) over a long period of time without sacrificing its activity.

The process for producing a microcapsule containing a liquid active material according to the present invention comprises the steps of:

(1) dissolving in an organic solvent a polymer, an active material which has a limited solubility in the polymer and which is liquid at room temperature (e.g., about 20° to 30° C.), and optionally an antioxidant, the organic solvent being capable of dissolving the respective components and being more volatile than the active material;

(2) atomizing the resulting solution through a nozzle into a gaseous atmosphere to form a mist of tiny liquid droplets; and (3) removing the solvent from the liquid droplets by evaporation so as to provide a microcapsule having the liquid active material confined by the wall of the microcapsule made of the polymer.

DETAILED DESCRIPTION OF THE INVENTION

Figure 1:
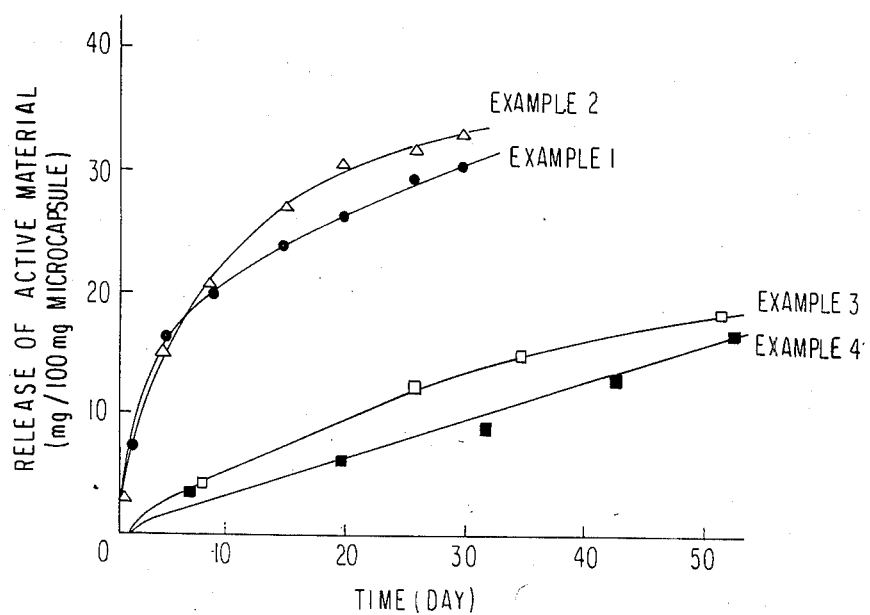
FIGS. 1 and 2 are graphs showing time-dependent profiles of the release of liquid active materials from various samples of microcapsules prepared by the process of the present invention.

A "liquid active material" according to the present invention means a substance that is liquid at room temperature and which has chemical or physiological activities such as agrichemical, attracting, repelling, or aromatic activities. The liquid active material may be oily or aqueous.

Examples of the liquid active material include agrichemically active materials such as insecticides (e.g., naled, diazinon and sumithion), and bactericides (e.g., $\beta$-propiolactone); repellants such as triethylene glycol monohexylether and N,N-diethyl-m-toluamide; attractants such as dodecyl acetate, Z-11-tetradecenyl acetate, Z-9-dodecenyl acetate and Z-11-hexadecenal; and aromatic active substances such as esters, ethers and aldehydes derived from hydrocarbons having 6 to 16 carbon atoms.

The microcapsule according to the present invention may have only the liquid active material confined therein. If the liquid active material has an aldehyde group, an antioxidant may also be confined in the microcapsule in order to effectively prevent the deterioration of the liquid active material so that it retains the intended activity. Therefore, the use of an antioxidant is particularly effective for ensuring a sustained and prolonged release of an aldehyde-containing, chemically unstable liquid active material, such as typically pheromone. Other examples of the aldehyde-containing active material include bactericides such as formothion; attractants such as E-11-tetradecenal, Z-11-tetradecenal, Z-9-tetradecenal, Z-11-hexadecenal, Z-11-octadecenal and Z,Z,Z-9,12,15-octadecatrienal; and aldehydes derived from hydrocarbons having 6 to 16 carbon atoms.

Thus, the microcapsule according to the present invention contains at least the liquid active material, and may contain an antioxidant used to prevent the deterioration of this liquid active material, the antioxidant being selected depending upon the type and properties of the liquid active material. Generally, antioxidants which are highly miscible with the liquid active material are selected. The antioxidant is generally used in an amount of from about 0.1 to about 20 wt %, and preferably from 1 to 15 wt %, based on the weight of the active material. Examples of the antioxidant include phenolic compounds, such as 1,6-di-t-butyl-4-methylphenol and alkylated bisphenol; phosphite compounds, such as trisnonylphenyl phosphite and triphenyl phosphite; imidazole compounds such as 2-mercaptobenzimidazole; thiodipropionate compounds such as distearly-3,3'-thiodipropionate and diallyl-3,3'-thiodipropionate; amine compounds such as nonylated diphenylamine and N,N'-diallyl-p-phenylenediamine; and propionate compounds such as n-octadecyl-3-(3',5'-di-t-butyl-4-hydroxyphenyl)propionate. These antioxidants may be used either alone or in combination.

The liquid active material used in the present invention must have a limited solubility in the film-forming polymer; the term "solubility" means the number of parts by weight of the liquid active material that can be dissolved in 100 parts by weight of the polymer. The terminology "limited solubility" as used herein means that about 0.01 to about 2 parts by weight of the active material dissolves in 100 parts by weight of the polymer. Therefore, at least about 2 parts by weight of the liquid active material is added per 100 parts by weight of the polymer, and the desired microcapsule can be obtained even if up to about 250 parts by weight of the active material is added. Preferably, the liquid active material is added in an amount of from about 10 parts by weight to about 200 parts by weight per 100 parts by weight of the polymer, and most preferably, the liquid active material is added in an amount of from about 40 parts by weight to about 150 parts by weight per 100 parts by weight of the polymer.

The polymer used in the present invention is properly selected depending upon the type of the liquid active material. Of various polymers which can be used in the present invention, glassy thermoplastics are preferred. Examples of the polymers include polysulfone, polyether sulfone, polyallyl ether, polyphenylene oxide, polyphenylene sulfide, polyester, polycarbonate, polystyrene, acrylonitrile-styrene copolymer, acrylonitrile-butadiene-styrene copolymer, polymethyl (meth)acrylate, polyamide, polyimide, polyvinylidene chloride, polyvinylidene fluoride, cellulose ester, regenerated cellulose, polyurethane, polyvinyl alcohol, polyvinyl chloride, polyvinyl acetate, ethylenevinyl acetate copolymer, vinyl chloride-vinyl acetate copolymer, and polystyrene-polybutadiene block copolymer. These polymers may be used either alone or in combination.

The organic solvent used in the process of the present invention must be such that it is capable of dissolving the film-forming polymer, liquid active material, and the optional antioxidant. The other requirement for the solvent is that it be more volatile (i.e., have a lower boiling point) than the liquid active material. The selection of the organic solvent depends on the type of the polymer, liquid active material, and antioxidant. Examples of the organic solvents include lower aliphatic halogenated hydrocarbons such as methylene chloride, chloroform and carbon tetrachloride; lower aliphatic alcohols such as methanol and ethanol, and acetate esters thereof; as well as acetonitrile, acetone, ethyl ether, and tetrahydrofuran. These organic solvents may be used either alone or in combination. Lower aliphatic halogenated hydrocarbons such as methylene chloride are preferred.

According to the process of the present invention, the liquid active material and the film-forming polymer, and optionally an antioxidant are dissolved in the organic solvent, and the resulting solution is passed through nozzle orifices into a gaseous atmosphere wherein the organic solvent is removed from the tiny droplets of the solution by evaporation. The total concentration of the liquid active material and polymer (and antioxidant, if present) in the solution formed in step (1) generally ranges from about 1.0 to about 50 wt %, preferably from about 1.5 to about 30 wt %, based on the total weight of the solution.

The evaporation of the organic solvent may be generally effected at room temperature, but if desired, elevated temperatures and/or vacuum conditions may be employed. The nozzle orifices are selected from their diameter depending upon the size of the intended microcapsule. Although not critical, the hole diameter of the nozzle ranges from about 0.1 to about 1 mm, preferably from about 0.4 to about 0.8 mm. As the evaporation of the organic solvent from the liquid droplets proceeds, a phase separation occurs between the polymer and the liquid active material having only a limited solubility in the polymer. As a result, the polymer forms a film that provides a wall for confining the liquid active material and optionally the antioxidant. The thus obtained microcapsule has a particle size of about 1 to about 200 μm, with a wall thickness generally being in the range of about 1/10 to about 1/100 of the capsule size.

According to the process of the present invention, the formation of a microcapsule is conducted in a gaseous atmosphere, and water does not enter the microcapsule, which is advantageous over conventional methods wherein the microcapsule is dried in the water and unavoidably absorbs at least some water. Therefore, the liquid active material confined in the microcapsule is protected from deterioration by water. Better protection against the deterioration of the liquid active material can be realized by confining an antioxidant as well as the liquid active material in the microcapsule, and this allows the liquid active material to exhibit its activity consistently over a long period of time.

Any film-forming polymer can be used so long as it permits only slow dissolution and elimination of the liquid active material from the interior of the microcapsules. The organic solvent may also be selected from a wide variety of compounds which are capable of dissolving not only the polymer and liquid active material, but also the antioxidant (if used), and which are more volatile than the liquid active material. According to the conventional methods, a water-soluble polymer must be used as a film-forming material even if the liquid active material is an oil. However, the present invention permits the use of an oil-soluble polymer in combination with an oily liquid active material.

The microcapsule prepared by the present invention has the liquid active material confined therein, preferably together with an antioxidant. Since the liquid active material has a limited solubility in the film-forming polymer, the former will not easily diffuse into the surrounding wall, and hence the sustained release of the liquid active material is ensured without sacrificing the effectiveness of the liquid active material. Therefore, the microcapsule according to the present invention enables the liquid active material to be released into an ambient atmosphere (temperature of 30°±15° C.) at a controlled, substantially constant rate while retaining the effectiveness of the liquid active material. Thus, the microcapsule can be advantageously used as a "slow-release" device for various liquid active materials.

The advantages of the present invention will become more apparent by reading the following working examples, to which the scope of the invention is by no means limited.

EXAMPLE 1

One gram of polysulfone ("P-1700", a product of Union Carbide Corporation) was dissolved in 100 ml of methylene chloride. 1 ml of an insect attractant (Z-9-dodecenyl acetate) was further added thereto, and the resulting mixture was agitated to form a uniform solution. The solution was atomized downward from the upper portion of a cylindrical vessel having a diameter of 50 cm and a height of 3 m through nozzle orifices in the form of liquid droplets having a particle size of 30 to 40 μm at room temperature. By evaporating the organic solvent, microcapsules having a particle size of 1 to 10 μm containing about 40 wt % of the active material were recovered from the bottom of the vessel. The microcapsules were allowed to stand in an open atmosphere at 30° C., and the time-dependent profile of the release of the active material was determined by checking the decrease in the weight of the microcapsules. The results obtained are shown in FIG. 1. The release of the active material from these microcapsules was sustained for at least 30 days, and 75% of the initially encapsulated active material had been released when 30 days passed.

The solubility of the Z-9-dodecenyl acetate was such that 0.4 part by weight thereof dissolved in 100 parts by weight of the polysulfone.

EXAMPLE 2

The same procedure as in Example 1 was repeated except that 1 ml of the insect attractant (Z-11-tetradecenyl acetate) was used as the liquid active material. Microcapsules having a particle size of 1 to 10 μm that contained about 40 wt % of the active material were produced. The time-dependent profile of the release of the active material was determined in the same manner as in Example 1, and the results obtained are shown in FIG. 1. The release from the microcapsules was sustained for at least 30 days, and 75% of the initially encapsulated active material had been released when 30 days passed.

The solubility of the Z-11-tetradecenyl acetate was such that 0.6 part by weight thereof dissolved in 100 parts by weight of the polysulfone.

EXAMPLE 3

The same procedure as in Example 1 was repeated except that 1 ml of the insecticide (diazinon) was used as the liquid active material, and that a polycarbonate ("Merlon", a product of Mobay Chemical Co.) was used as the film-forming polymer. Microcapsules having a particle size of 1 to 10 μm that contained about 50 wt % of the active material were produced. The time-dependent profile of the release of the active material was determined in the same manner as in Example 1, and the results obtained are shown in FIG. 1. The release from the microcapsules was sustained for at least 50 days, and about 40% of the initially encapsulated active material had been released when 50 days passed.

The solubility of the diazinon was such that 2 parts by weight thereof dissolved in 100 parts by weight of the polycarbonate.

EXAMPLE 4

The same procedure as in Example 1 was repeated except that 1 ml of the insecticide (naled) was used as the liquid active material and that the same polycarbonate as was used in Example 3 was used as the film-forming polymer. Microcapsules having a particle size of 1 to 10 μm that contained about 50 wt % of the active material were produced. The time-dependent profile of the release of the active material was determined in the same manner as in Example 1, and the results obtained are shown in FIG. 1. The release from the microcapsules continued for at least 100 days, and about 30% of the initially encapsulated active material had been released when 50 days passed.

The solubility of the naled was such that 2 parts by weight thereof dissolved in 100 parts by weight of the polycarbonate.

EXAMPLE 5

Four grams of polysulfone, which was the same as that used in Example 1, was dissolved in 100 ml of methylene chloride, and then, 4 ml of Z-11-hexadecenal was added thereto. The resulting mixture was agitated to form a uniform solution. The solution was atomized through nozzle orifices into a gaseous atmosphere at room temperature so as to obtain liquid droplets having a particle size of 30 to 40 $\mu$m. By evaporating the organic solvent, microcapsules having a particle size of 1 to 20 $\mu$m that contained about 40 wt % of the active material were formed.

Figure 2:
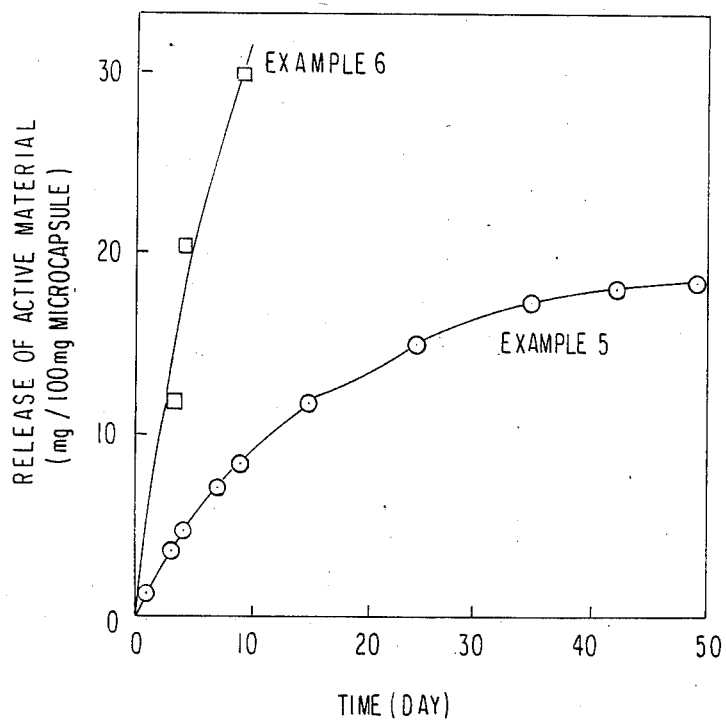

The time-dependent profile of the release of the active material was determined in the same manner as in Example 1, and the results obtained are shown in FIG. 2. The release from the microcapsules continued for at least 50 days, and 50% of the initially encapsulated active material had been released when 50 days passed.

EXAMPLE 6

Six grams of polymethyl methacrylate ("Plexiglas", a product of Rohm and Haas Company) was dissolved in 100 ml of methylene chloride, and then, 12 ml of Z-11-tetradecenyl acetate was added thereto. The resulting mixture was agitated to form a uniform solution. The solution was atomized through nozzle orifices into a gaseous atmosphere at room temperature so as to obtain liquid droplets having a particle size of 30 to 40 $\mu$m. By evaporating the organic solvent, microcapsules having a particle size of 1 to 50 $\mu$m that contained about 65 wt % of the active material were formed.

The time-dependent profile of the release of the active material was determined in the same manner as in Example 1, and the results obtained are shown in FIG. 2. When 10 days had passed, 50% of the initially encapsulated active material was found to have been released from the microcapsules.

EXAMPLE 7

Four grams of a polysulfone ("P-1700", a product of Union Carbide Corporation) was dissolved in 100 ml of methylene chloride. 4 ml of an insect attractant (z-11-hexadecenal) and 0.4 g of an antioxidant (2,6-di-t-butyl-4-methylphenol) were further added, and the resulting mixture was agitated to form a uniform solution. The solution was atomized through nozzle orifices into a gaseous atmosphere at room temperature so as to obtain liquid droplets having a particle size of 30 to 40 $\mu$m. By evaporating the organic solvent, microcapsules having a particle size of 1 to 20 $\mu$m were obtained, and they contained about 40 wt % of the active material and about 5 wt % of the antioxidant.

The solubility of the Z-11-hexadecenal was such that 0.7 part by weight thereof dissolved in 100 parts by weight of the polysulfone.

Figure 3:
FIG. 3 is an electron micrograph showing a cross sectional view of the microcapsules having a liquid active material confined therein according to the present invention.

The scanning electron micrograph (X7650) of the cross-sectional view of the microcapsules prepared in Example 7 is shown in FIG. 3. It can easily be seen from FIG. 3 that these microcapsules have a particle size ranging from 1 to 20 $\mu$m.

Figure 4:
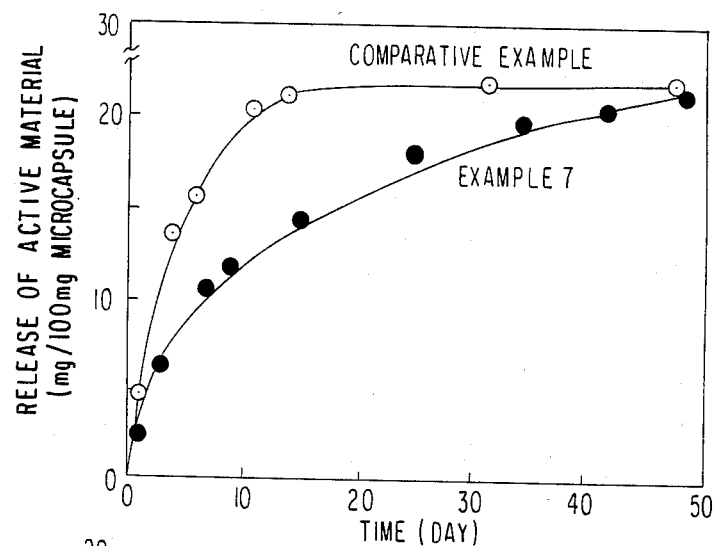
FIGS. 4 and 5 are graphs showing the time-dependent profiles of the release of liquid active materials from other samples of the microcapsules according to the present invention, as compared with the release profile for a comparative sample.

The microcapsules obtained above were allowed to stand in an open atmosphere at 30° C., and the time-dependent profile of the release of the active material was determined in the same manner as in Example 1. The results obtained are shown in FIG. 4. Under the mild conditions employed, the active material remained stable within the microcapsules and could be released consistently at a controlled rate over a period of 50 days.

Figure 5:
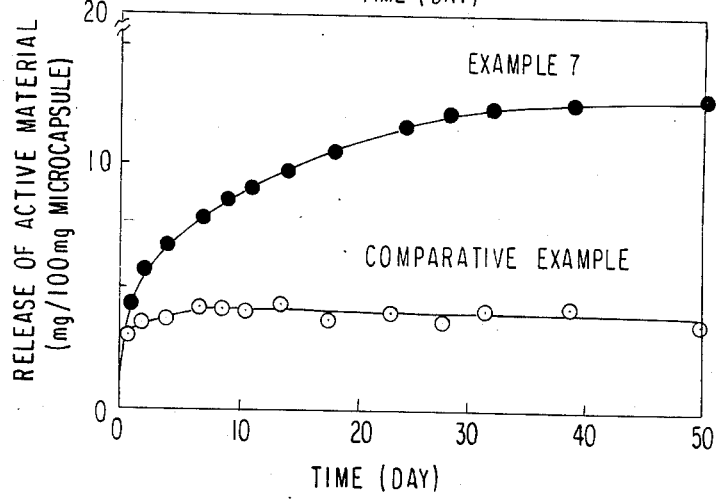
Figure 6:
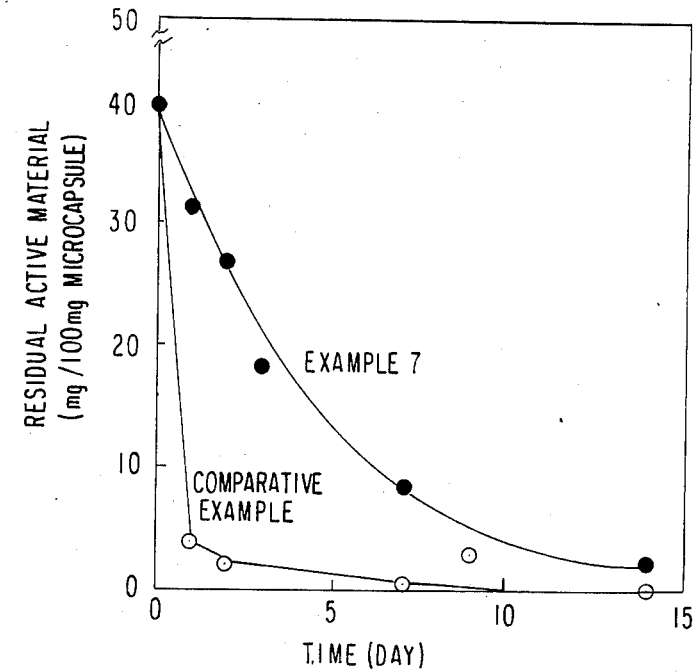
FIG. 6 is a graph showing the time-dependent change in the residual amount of liquid active material from the microcapsules according to the present invention, as compared with the data for the comparative sample.

Further, the microcapsules were placed under irradiation with UV rays at 40° C., and the time-dependent profile of the release of the active material was determined by the same method indicated above. The results obtained are shown in FIG. 5. It can be seen from FIG. 5 that even under the severe conditions used, the active material could be released from the microcapsules over a long period of time. Under same severe conditions, the time-dependent change in the residual amount of Z-11-hexadecenal in the microcapsules was checked. The results obtained are shown in FIG. 6. It can be seen from FIG. 6 that about 5 wt % of the active material remained in the microcapsules of the present invention even after the lapse of 10 days.

COMPARATIVE EXAMPLE

As a comparative sample, microcapsules were prepared by the following conventional method. One gram of polysulfone, which was the same as used in Example 7, was dissolved in 10 ml of methylene chloride. Then, 1 ml of Z-11-hexadecenal and 0.1 g of an antioxidant (2,6-di-t-butyl-4-methylphenol) were added. The resulting mixture was agitated to form a uniform solution. The solution was dispersed in 1,000 ml of a 1 wt % aqueous gelatin solution at room temperature so as to form an emulsion. The emulsion was heated to 45° C., at which temperature the emulsion was continuously agitated to remove the organic solvent by evaporation. By these procedures, microcapsules having a particle size of about 10 $\mu$m containing about 40 wt % of the active material and about 5 wt % of the antioxidant were produced.

The time-dependent profile of the active material from the microcapsules at 30° C. was determined in the same manner as in Example 7. The results obtained are shown in FIG. 4. It can be seen from FIG. 4 that even under the mild conditions used, the release of the active material from the comparative sample of microcapsules could not be continued for more than 15 days.

The comparative microcapsules were placed under irradiation with UV rays at 40° C. and the time-dependent profile of the release of the active material was determined by the same method as described above. The results obtained are shown in FIG. 5. Under the severe conditions used, the release of the active material from the comparative microcapsules continued for only 2 days. Under same severe conditions, the time-dependent change in the residual amount of Z-11-hexadecenal in the microcapsules was checked. The results obtained are shown in FIG. 6. It can be seen from FIG. 6 that the residual amount of Z-11-hexadecenal dropped to 5 wt % or less within one day.

EXAMPLE 8

Four grams of polysulfone, which was the same as used in Example 1, was dissolved in 100 ml of methylene chloride. Then, 4 ml of an insect attractant (Z-11-tetradecenal) and 0.4 g of an antioxidant (2.6-di-t-butyl-4-methylphenol) were added. The resulting mixture was agitated to obtain a uniform solution. The solution was atomized through nozzle orifices into a gaseous atmosphere at room temperature, so as to obtain liquid droplets having a particles size of 30 to 40 μm. As in Example 7 microcapsules capsules having a particle size of 1 to 20 μm containing about 40 wt % of the active material and about 5 wt % of the antioxidant were produced.

The solubility of the Z-11-tetradecenal was such that 0.7 part by weight thereof dissolved in 100 parts by weight of the polysulfone.

The microcapsules were allowed to stand under irradiation with UV rays at 40° C. Even under such severe conditions, the active material could be consistently released from the microcapsules to a controlled rate over a period of 15 days.

While the invention has been described in detail and with reference to specific embodiments thereof, it will be apparent to one skilled in the art that various changes and modifications can be made therein without departing from the spirit and scope thereof.

What is claimed is:

1. A process for producing a microcapsule containing a liquid active material, which can release the liquid material into an ambient atmosphere (30°±15° C.) at a controlled rate, comprising the steps of:

(1) dissolving in an organic solvent a polysulfone and an active material which has a limited solubility of about 0.01 to about 2 parts by weight in 100 parts by weight of said polysulfone and which is liquid at room temperature, the amount of said liquid active material added being more than the limited solubility and being about 2 to about 250 parts by weight per 100 parts by weight of the polysulfone and said organic solvent being capable of dissolving the respective components and being more volatile than said active material;

(2) atomizing the resulting solution through a nozzle into a gaseous atmosphere to form a mist of tiny liquid droplets; and (3) removing the solvent from the droplets by evaporation so as to provide a microcapsule having the liquid active material confined by the wall of said microcapsule made of the polysulfone.

2. A process as in claim 1 wherein an antioxidant is additionally dissolved in the organic solvent in step (1).

3. A process as in claim 2, wherein the liquid active material has an aldehyde group and the antioxidant is added in an amount of from about 0.1 to about 20 wt % based on the weight of the liquid active material.

4. A process as in claim 3, wherein the amount of the antioxidant is from about 1 to about 15 wt % based on the weight of the liquid active material.

5. A process as in claim 2, wherein the antioxidant is at least one member selected from the group consisting of a phenolic antioxidant; a phosphite antioxidant; an imidazole antioxidant; a thiodipropionate antioxidant; an amine antioxidant; and a propionate antioxidant.

6. A process as in claim 5, wherein the antioxidant is added in an amount of from about 0.1 to about 20 wt % based on the weight of the liquid active material.

7. A process as in claim 5, wherein the antioxidant is added in an amount of from about 1 to about 15 wt % based on the weight of the liquid active material.

8. A process as in claim 2, wherein the antioxidant is at least one member selected from the group consisting of 2,6-di-t-butyl-4-methylphenol, alkylated bisphenol, trisnonylphenyl phosphite, triphenyl phosphite, 2-mercaptobenzimidazole, distearyl-3,3'-thiodipropionate, diallyl-3,3'-thiodipropionate, nonylated diphenylamine, N,N'-diallyl-p-phenylenediamine and n-octadecyl-3-(3',5'-di-t-butyl-4-hydroxyphenyl)propionate.

9. A process as in claim 2, wherein the total concentration of the liquid active material and polysulfone in the solution formed in step 1 ranges from about 1.0 to about 50 wt %, based on the total weight of the solution.

10. A process as in claim 2, wherein the total concentration of the liquid active material and polysulfone in the solution formed in step 1 ranges from about 1.5 to about 30 wt %, based on the total weight of the solution.

11. A process as in claim 1, wherein the liquid active material is a substance that is liquid at room temperature and which has chemical or physiological activities comprising agrichemical, attracting, repelling, or aromatic activities.

12. A process as in claim 11, wherein the liquid active material is insecticide, bactericide, repellant, attractant or aromatic active substance.

13. A process as in claim 12, wherein the attractant is insect attractant.

14. A process as in claim 1, wherein the easily volatile organic solvent is at least one member selected from the group consisting of a lower aliphatic halogenated hydrocarbon, a lower aliphatic alcohol or an acetate ester thereof, acetonitrile, acetone, ethyl ether and tetrahydrofuran.

15. A process as in claim 1, wherein the total concentration of the liquid active material and polysulfone in the solution formed in step 1 ranges from about 1.0 to about 50 wt %, based on the total weight of the solution.

16. A process as in claim 1, wherein the total concentration of the liquid active material and polysulfone in the solution formed in step 1 ranges from about 1.5 to about 30 wt %, based on the total weight of the solution.

* * * * *